US011491084B2

(12) United States Patent
Ueda et al.

(10) Patent No.: US 11,491,084 B2
(45) Date of Patent: Nov. 8, 2022

(54) MEDICAL DEVICE

(71) Applicant: TERUMO KABUSHIKI KAISHA, Tokyo (JP)

(72) Inventors: Yasuhiro Ueda, Kofu (JP); Kazuya Akiyama, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 393 days.

(21) Appl. No.: 16/915,284

(22) Filed: Jun. 29, 2020

(65) Prior Publication Data

US 2020/0323734 A1    Oct. 15, 2020

Related U.S. Application Data

(63) Continuation of application No. PCT/JP2019/006623, filed on Feb. 21, 2019.

(30) Foreign Application Priority Data

Mar. 27, 2018 (JP) .............................. JP2018-060303

(51) Int. Cl.
*A61J 1/20*   (2006.01)
*A61M 39/26*   (2006.01)

(52) U.S. Cl.
CPC .............. *A61J 1/201* (2015.05); *A61M 39/26* (2013.01)

(58) Field of Classification Search
CPC ...... A61M 36/26; A61J 1/2051; A61J 1/2037; A61J 1/2065; A61J 1/2089; A61J 1/2093; A61J 1/2096; A61J 1/2048
See application file for complete search history.

(56) References Cited

U.S. PATENT DOCUMENTS 5,826,713 A * 10/1998 Sunago .................. A61J 1/2089
                                                                 206/219
6,113,068 A *  9/2000 Ryan .................... A61M 39/045
                                                                 604/905

(Continued)

FOREIGN PATENT DOCUMENTS

WO    WO 2009/133754     11/2009
WO    WO 2012/117648 A1   9/2012

(Continued)

OTHER PUBLICATIONS

International Search Report for International Application No. PCT/JP2019/006623, dated Mar. 19, 2019.

(Continued)

*Primary Examiner* — Catharine L Anderson
*Assistant Examiner* — Arjuna P Chatrathi
(74) *Attorney, Agent, or Firm* — Sheridan Ross, PC

(57) ABSTRACT

Medical devices are provided comprising a spike including proximal and distal ends, and a central axis extending from the proximal to the distal end; a valve body; a biasing body which biases the valve body; a distal tube that moves integrally with the valve body to both sides in the axial direction relative to the spike; a proximal tube fixed in the axial direction relative to the spike, the distal tube comprising a guided portion guided toward the proximal tube, and an engagement control unit which moves the guided portion toward one side in the radial direction by connection of the different medical device to the distal tube allowing the guided portion to engage with the proximal tube, and moves the guided portion toward the other side in the radial direction releasing engagement with the proximal tube when the different medical device is detached from the distal tube.

20 Claims, 13 Drawing Sheets

(56) References Cited

U.S. PATENT DOCUMENTS

| | | |
|---|---|---|
| 8,157,784 B2 | 4/2012 | Rogers |
| 2011/0074148 A1* | 3/2011 | Imai ..................... A61M 39/26 |
| | | 285/308 |
| 2012/0179128 A1* | 7/2012 | Takemoto ................. A61J 1/20 |
| | | 604/414 |
| 2019/0184152 A1 | 6/2019 | Kakinoki |

FOREIGN PATENT DOCUMENTS

| | | |
|---|---|---|
| WO | WO 2018/056465 | 3/2018 |
| WO | WO 2018/174265 A1 | 9/2018 |

OTHER PUBLICATIONS

Written Opinion for International Application No. PCT/JP2019/006623, dated Mar. 19, 2019.
Notice of Reasons for Refusal (Including Translation) for corresponding Japanese Patent Application No. 2020-510438, dated May 10, 2022.
International Preliminary Report on Patentability for International Application No. PCT/JP2019/006623, dated Sep. 29, 2020.

\* cited by examiner

MEDICAL DEVICE

CROSS REFERENCE TO RELATED APPLICATIONS

The present application is a continuation of and claims benefit to PCT Application No. PCT/JP2019/006623, filed on Feb. 21, 2019, entitled "MEDICAL INSTRUMENT" which claims priority to Japanese Patent Application No. 2018-060303, filed on Mar. 27, 2018. The entire disclosures of the applications listed above are hereby incorporated herein by reference, in their entirety, for all that they teach and for all purposes.

FIELD

The present disclosure relates to medical devices and, in particular, toward medical connectors.

BACKGROUND

A medical connector or a syringe may correspond to medical devices used for infusion, or the like, into a living body such as a human body. Such medical devices may include a closed connector portion provided with a valve body. For example, a medical device disclosed in FIG. 9 of U.S. Pat. No. 8,157,784 includes a connector unit provided with a spike including an inner flow path, a valve body, a biasing body which biases the valve body, a distal tube to which a different medical device is able to be connected and which is capable of moving integrally with the valve body to both sides in an axial direction of the spike, and a proximal tube integrally coupled with the spike.

SUMMARY

According to the medical device disclosed in U.S. Pat. No. 8,157,784, it is possible to reduce a possibility that an operator erroneously touches fluid when performing an operation of establishing fluid connection to a different medical device or releasing the same in order to form or remove an infusion line. This effect is especially important when a harsh or potentially toxic medicine, such as an anticancer drug, is used as the fluid.

By the way, in such medical device, in order to stabilize an operation of the distal tube when the distal tube moves to both the sides in the axial direction of the spike relative to the proximal tube, it is required that a guided portion guided toward the proximal tube along with the movement be provided on the distal tube. However, when such guided portion is provided, when a different medical device is unintentionally detached from the distal tube by an external force or the like in a fluid connection state, there is a possibility that the distal tube does not return to a distal end side and the inner flow path of the spike is exposed from the valve body to expose the fluid due to engagement of the guided portion with the proximal tube.

In view of the problems outlined above, an object of the present disclosure is to provide a medical device capable of reducing a possibility of exposing fluid even when a different medical device is unintentionally detached in a fluid connection state with the different medical device.

A medical device as a first aspect of the present disclosure is provided with: a spike including a proximal end, a distal end, a central axis extending from the proximal end to the distal end, and an inner flow path; a valve body through which the spike is able to pass; a biasing body which biases the valve body toward a side of the distal end in an axial direction along the central axis; a distal tube to which a different medical device is able to be connected, the distal tube capable of moving integrally with the valve body to both sides in the axial direction relative to the spike; and a proximal tube which is not able to move to both the sides in the axial direction relative to the spike, the distal tube is provided with a guided portion guided toward the proximal tube along with movement to both the sides in the axial direction, the medical device is further provided with: an engagement control unit which moves the guided portion toward one side in the radial direction by connection of the different medical device to the distal tube to allow the guided portion to engage with the proximal tube, and moves the guided portion toward the other side in the radial direction to release engagement with the proximal tube when the different medical device is detached from the distal tube.

As one embodiment of the present disclosure, the distal tube is arranged on an inner side in the radial direction relative to the proximal tube.

As one embodiment of the present disclosure, the medical device is provided with a pusher capable of moving to both the sides in the axial direction relative to the distal tube as the engagement control unit, in which the pusher elastically displaces the guided portion radially outward to allow the guided portion to engage with the proximal tube by moving to a side of the proximal end in the axial direction relative to the distal tube by pressure from the different medical device along with the connection of the different medical device to the distal tube.

As one embodiment of the present disclosure, the different medical device includes a different valve body and a different inner flow path, it is possible to shift, or transition, from a standby state in which the different medical device is connected to the distal tube, the different valve body abuts the valve body, and the spike does not pass through the valve body and the different valve body to a fluid connection state in which the different medical device is connected to the distal tube, the different valve body abuts the valve body, and the spike passes through both the valve body and the different valve body and the inner flow path is communicated with the other inner flow path by a predetermined fluid connection operation, and shift, or transition, from the fluid connection state to the standby state by a predetermined releasing operation.

As one embodiment of the present disclosure, the proximal tube guides the guided portion toward the side of the proximal end in the axial direction by a rotational operation to one side in a circumferential direction regarding the central axis as the predetermined fluid connection operation, and guides the guided portion toward the side of the distal end in the axial direction by a rotational operation to the other side in the circumferential direction as the predetermined releasing operation.

According to the present disclosure, it is possible to provide a medical device capable of reducing a possibility of exposure of the fluid even when a different medical device is unintentionally detached in the fluid connection state with the different medical device.

DETAILED DESCRIPTION

Figure 1:
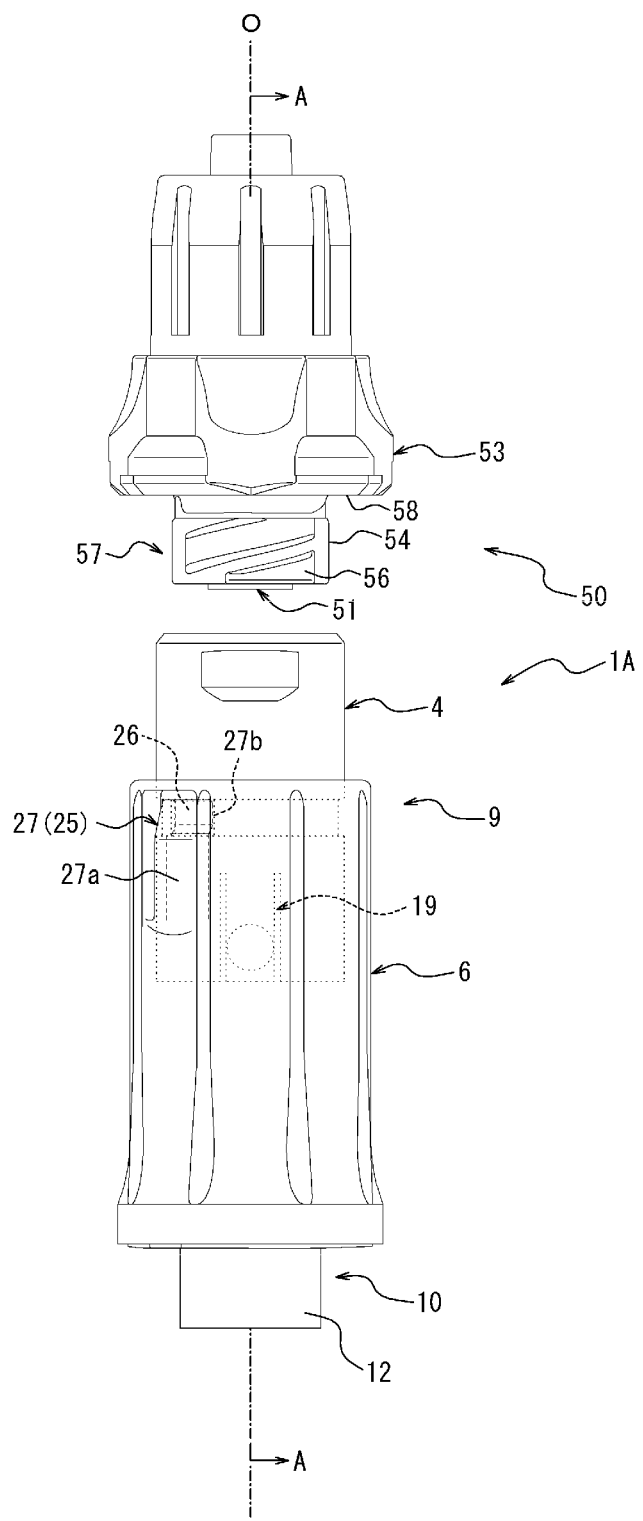
FIG. 1 is a side view illustrating a medical device according to a first embodiment of the present disclosure in an unconnected state to a different medical device.
Figure 2:
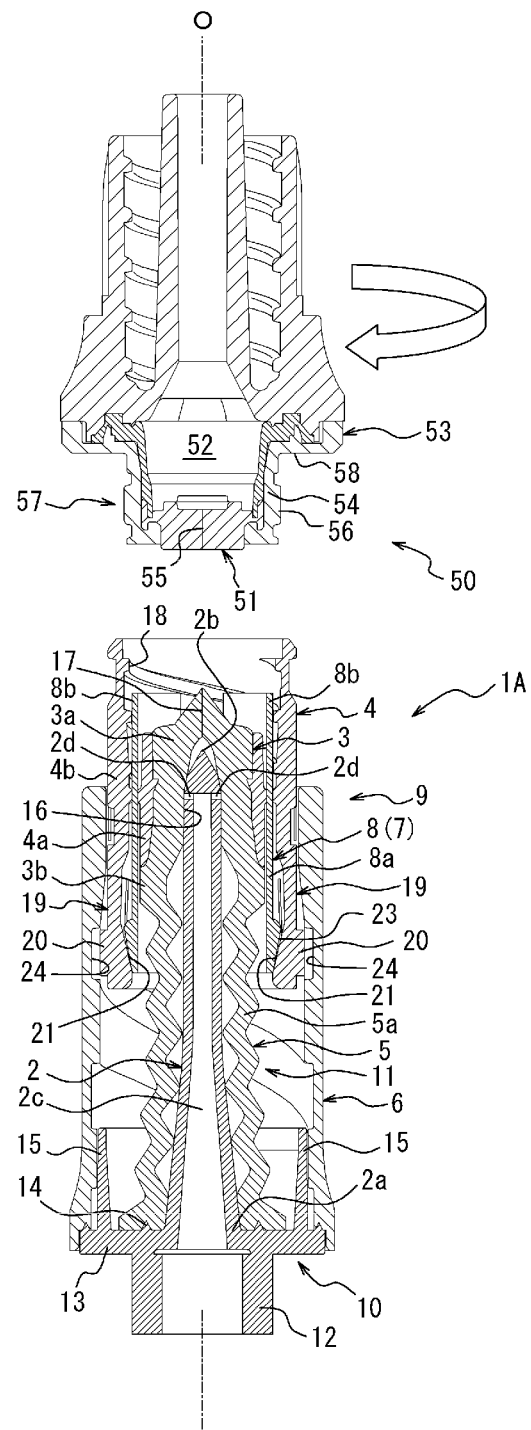
FIG. 2 is a cross-sectional view taken along line A-A of FIG. 1.
Figure 3:
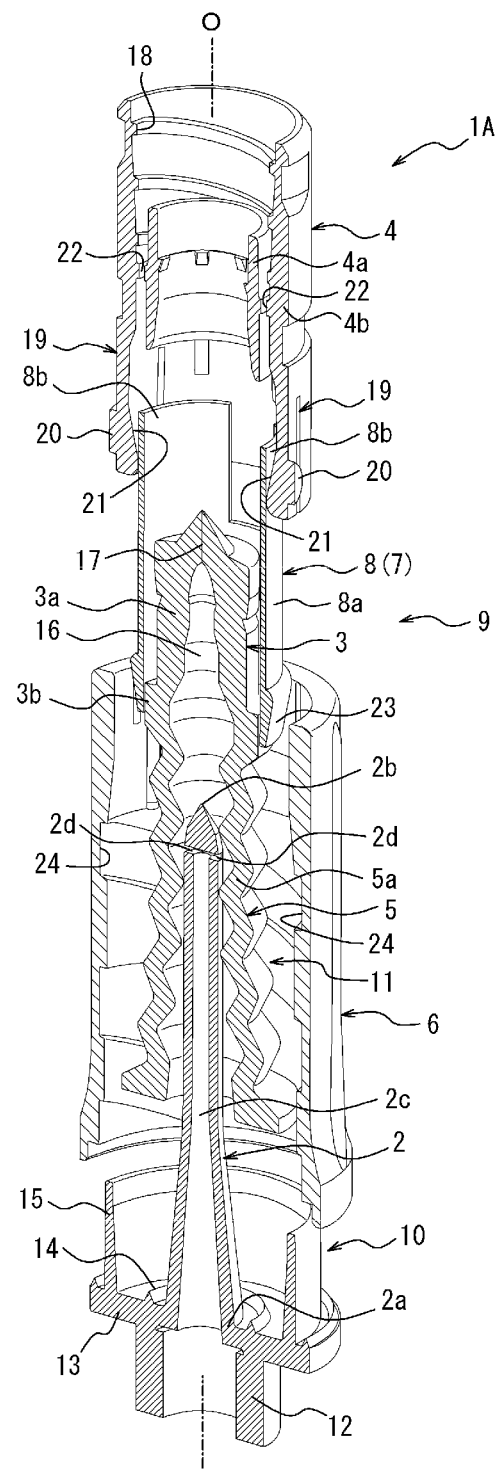
FIG. 3 is an exploded perspective cross-sectional view of the medical device illustrated in FIG. 1.

A medical device according to an embodiment of the present disclosure is hereinafter described with an example in detail with reference to the drawings. First, a medical device according to a first embodiment of the present disclosure is described with an example in detail with reference to FIGS. 1 to 9. As illustrated in FIGS. 1 to 3, a medical device 1A according to this embodiment includes a connector portion 9 provided with a spike 2, a valve body 3, a distal tube 4, a biasing body 5, a proximal tube 6, and a pusher 8 as an engagement control unit 7. The medical device 1A is formed as a medical connector including the connector portion 9. However, the medical device 1A is not limited to the medical connector, and may be formed as, for example, a syringe including the connector portion 9 (for example, a syringe including an outer tube provided with the connector portion 9 on an outlet on a distal end thereof and a pusher inserted into a proximal end of the outer tube).

The spike 2 is formed of a part of a spike member 10. Each of the spike member 10, the proximal tube 6, the distal tube 4, and the pusher 8 is formed as a single member formed by injection molding or the like of a synthetic resin or the like. However, each of the spike member 10, the proximal tube 6, the distal tube 4, and the pusher 8 may be formed of a plurality of members. The valve body 3 is formed of a head and a shoulder of a valve member 11, and the biasing body 5 is formed of a body of the valve member 11. The valve member 11 is formed as a single member formed by injection molding or the like of rubber, an elastomer, or the like. However, the valve body 3 and the biasing body 5 may also be formed as separate members. The spike member 10 and the proximal tube 6 are formed as separate members in this embodiment, but they may be formed as a single member.

The spike 2 includes a proximal end 2a, a distal end 2b, a central axis O extending from the proximal end 2a to the distal end 2b, an inner flow path 2c, and a communication port 2d communicated with the inner flow path 2c. In this disclosure, the term "axial direction" as used herein may refer to a direction along the central axis O. As used herein, the term "distal end side in the axial direction" may refer to a direction from a side of the proximal end 2a to a side of the distal end 2b in the axial direction, the term "proximal end side in the axial direction" may refer to a direction opposite to the "distal end side in the axial direction", and the term "both sides in the axial direction" may refer to both directions to the "distal end side in the axial direction" and "proximal end side in the axial direction". The term "distal end" regarding a predetermined portion may refer to an end located on the distal end side in the axial direction of the portion, and the term "proximal end" regarding a predetermined portion may refer to an end located on the proximal end side in the axial direction of the portion. The term "radial direction" may refer to a radial direction regarding the central axis O, and the term "circumferential direction" may refer to a circumferential direction regarding the central axis O. For convenience of description, regarding a predetermined portion, the distal end side in the axial direction may sometimes be referred to as an upper side, and the proximal end side in the axial direction may sometimes be referred to as a lower side. For example, an upper surface of the distal tube 4 means a surface as seen in a direction toward the proximal end side in the axial direction.

The spike 2 has a hollow cylindrical shape extending linearly in the axial direction, and the distal end 2b thereof has a sharp shape. The inner flow path 2c extends linearly in the axial direction from the proximal end 2a and terminates short of the distal end 2b. The communication port 2d is formed of two through-holes facing each other which pass through a wall surface of the spike 2 in the radial direction. The communication port 2d is in communication with the inner flow path 2c at a terminal of the inner flow path 2c. However, the shape of the spike 2 may be appropriately changed. For example, the spike 2 does not necessarily have to extend linearly. The distal end of the spike 2 does not have to be sharp. The number of through-holes forming the communication port 2d may be appropriately increased or decreased. The communication port 2d may also be in communication with the inner flow path 2c in a portion other than the terminal of the inner flow path 2c.

A distal end of a female connector portion 12 is coupled with the proximal end 2a of the spike 2. Male connector portions of various medical devices may be connected to the female connector unit 12 for the purpose of forming an infusion line or the like. An inner peripheral edge of an annular flange 13 extending in the radial direction is coupled with the proximal end 2a of the spike 2. An annular projection 14 which adheres to a lower surface of the biasing body 5 over an entire circumference of the central axis O is provided on an upper surface of the flange 13. A lower end of a cylindrical tube wall 15 is coupled with an outer side in the radial direction of the annular projection 14 on the upper surface of the flange 13. A proximal end portion of the proximal tube 6 is fixed to an outer peripheral edge of the flange 13 and an outer peripheral surface of the tube wall 15. Therefore, the proximal tube 6 cannot move to both the sides in the axial direction relative to the spike 2. However, it is sufficient that the proximal tube 6 cannot move to both the sides in the axial direction relative to the spike 2, and this may be attached to the spike member 10 so as to be rotatable in the circumferential direction, for example.

The valve member 11 includes the biasing body 5 which biases the valve body 3 toward the distal end side in the axial direction. The biasing body 5 is formed of a bellows portion 5a extending in the axial direction. The bellows portion 5a is configured to be elastically deformed so as to be folded and contracted in the axial direction when receiving a compression force in the axial direction and to be restored to its original shape when the compression force is removed. The biasing body 5 is not limited to that formed of the bellows portion 5a, and this may also be formed of, for example, elastic bodies having various shapes elastically deformed so as to contract in the axial direction when receiving the compression force in the axial direction and restored to its original shape when the compression force is removed. For example, the biasing body 5 may also be formed of a compression coil spring.

The valve member 11 includes the valve body 3 which surrounds the spike 2 from an outer side in the radial direction. The valve body 3 is formed of a hollow cylindrical valve main body 3a formed of the head of the valve member 11 and a valve flange 3b formed of the shoulder of the valve member 11. The valve main body 3a includes a hollow portion 16 capable of accommodating the distal end 2b of the spike 2 and its peripheral portion. A slit 17 is provided between an upper end of the hollow portion 16 and a top surface (upper surface) of the valve main body 3a. The valve main body 3a may close the communication port 2d in a state in which the communication port 2d of the spike 2 is located in any of the hollow portion 16 and the slit 17. The top surface of the valve main body 3a has a projection shape in which a central portion as seen from above projects in a conical shape. However, the shape of the top surface of the valve main body 3a may be appropriately changed. For example, the top surface of the valve main body 3a may have a spherical shape projecting upward. The valve flange 3b has a cylindrical shape an outer diameter of which is larger than that of the valve main body 3a. An upper end of the valve flange 3b is coupled with a lower end of the valve main body 3a, and a lower end of the valve flange 3b is coupled with an upper end of the biasing body 5. The shape of the valve flange 3b may be appropriately changed, and may also be, for example, a polygonal tubular shape (e.g., a polygonal tubular shape as seen from above).

The distal tube 4 is formed to be movable integrally with the valve body 3 to both the sides in the axial direction relative to the spike 2. The distal tube 4 includes a holding tube 4a attached to the valve body 3 to hold the valve body 3, an engaging tube 4b arranged on an outer side in the radial direction relative to the holding tube 4a, and a coupling portion 4c (refer to FIG. 5) which couples the holding tube 4a with the engaging tube 4b in the radial direction.

The holding tube 4a has a cylindrical shape. However, the holding tube 4a may also have a tubular shape other than the cylindrical shape in accordance with the shape of the valve body 3. An inner peripheral surface of the holding tube 4a fits to an outer peripheral surface of the valve main body 3a. However, it is also possible that the holding tube 4a does not fit to the valve main body 3a. For example, the holding tube 4a may be fixed to the valve main body 3a. The top surface of the valve body 3 may project from a distal end face of the holding tube 4a toward the distal end side. A distal end face of the valve flange 3b of the valve body 3 abuts a proximal end face of the holding tube 4a.

The engaging tube 4b has a cylindrical shape. However, the engaging tube 4b may also have any other tubular shape other than the cylindrical shape. A connecting portion 18 to a different medical device 50 is provided in a portion closer to a distal end side than the coupling portion 4c of the engaging tube 4b. In this embodiment, the connecting portion 18 is formed of a female screw portion capable of luer locking. However, the connecting portion 18 may also be formed of that other than such female screw portion. A pair of elastic arms 19 facing each other across the central axis O is provided in a portion closer to a proximal end side than the coupling portion 4c of the engaging tube 4b. The pair of elastic arms 19 has the same shape. However, the pair of elastic arms 19 may have different shapes.

Figure 4:
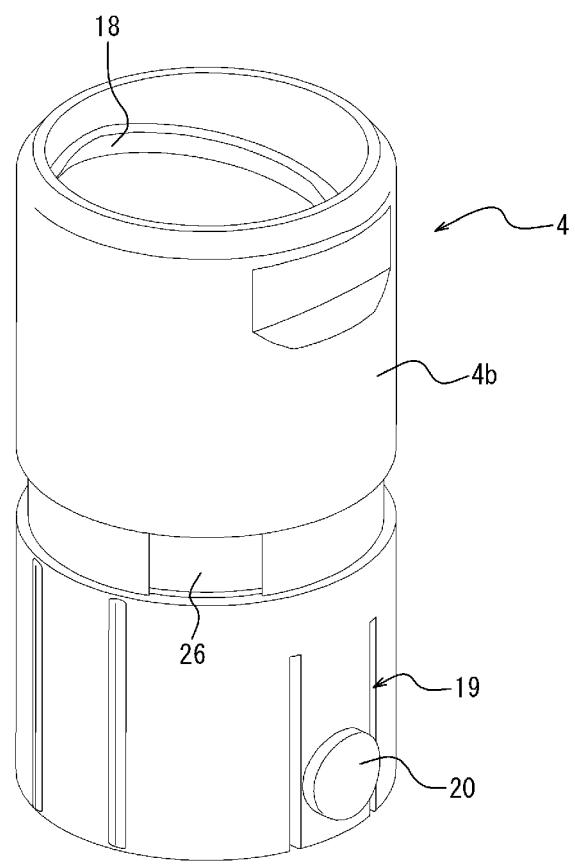
FIG. 4 is a perspective view of a distal tube illustrated in FIG. 1.

As illustrated in FIGS. 2 and 4, each elastic arm 19 has a cantilever shape divided by two parallel linear notches extending from the proximal end of the engaging tube 4b toward the distal end side in the axial direction. However, the shape of each elastic arm 19 is not limited to such one divided by the two parallel linear notches and may be changed as appropriate. On an outer surface (e.g., a surface on an outer side in the radial direction) of each elastic arm 19, a cylindrical engaging convex portion 20 projecting radially outward is provided. However, the shape of each engaging convex portion 20 is not limited to the cylindrical shape and may be appropriately changed. Each engaging convex portion 20 forms a guided portion guided toward the proximal tube 6 as this moves to both the sides in the axial direction. On an inner surface of each elastic arm 19, a pressed portion 21 projecting radially inward is provided. Each pressed portion 21 is formed of an inclined surface which inclines radially inward toward the proximal end side in the axial direction.

Figure 5:
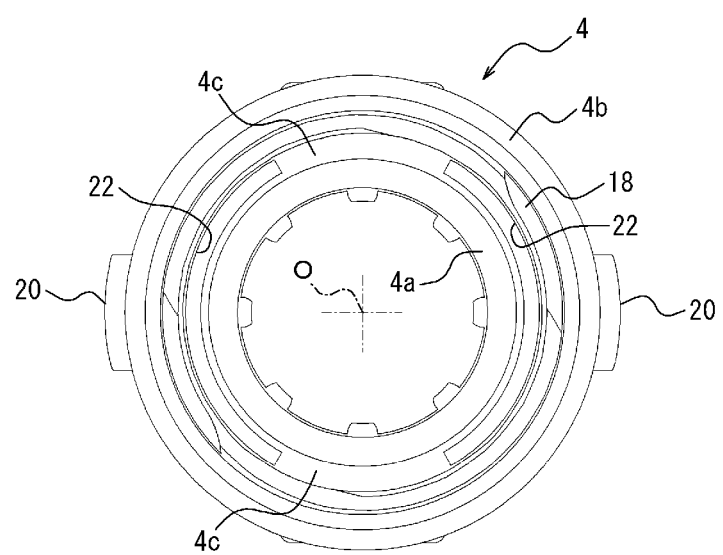
FIG. 5 is a top view of the distal tube illustrated in FIG. 1.

As illustrated in FIG. 5, the coupling portion 4c is provided intermittently in the circumferential direction. A pair of long holes 22 facing each other across the central axis O is provided on an intermittent portion of the coupling portion 4c. Each long hole 22 has an arc shape extending in the circumferential direction. The pair of long holes 22 has the same shape. However, the pair of long holes 22 may have different shapes. The shape of each long hole 22 is not limited to the arc shape and may be appropriately changed.

Figure 6:
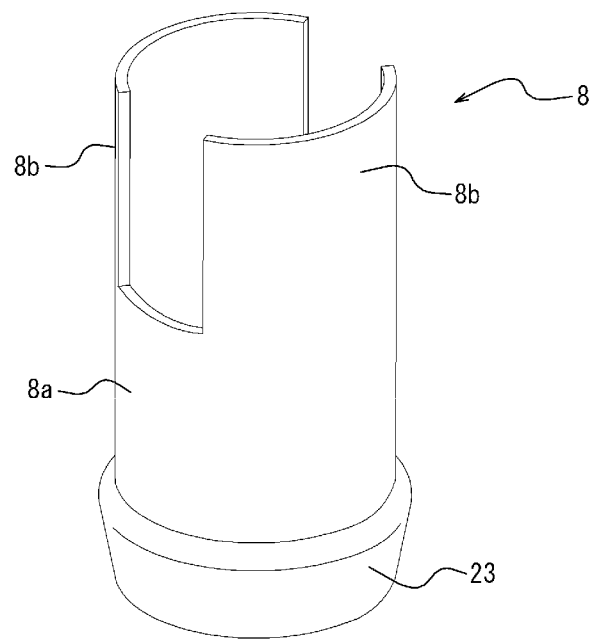
FIG. 6 is a perspective view of a pusher illustrated in FIG. 1.

The pusher 8 is movable to both the sides in the axial direction relative to the distal tube 4. As illustrated in FIGS. 2 and 6, the pusher 8 includes a cylindrical base body 8a and a pair of projecting bodies 8b extending from a distal end of the base body 8a toward the distal end side in the axial direction and facing each other across the central axis O. Each projecting body 8b has an arc shape extending in the circumferential direction. The pair of projecting bodies 8b has the same shape. However, the pair of projecting bodies 8b may have different shapes. One of the pair of projecting bodies 8b passes through one of the pair of long holes 22 provided on the distal tube 4 and projects from a distal end face of the holding tube 4a toward the distal end side in the axial direction. The other of the pair of projecting bodies 8b passes through the other of the pair of long holes 22 provided on the distal tube 4 and projects from the distal end face of the holding tube 4a toward the distal end side in the axial direction. The shape of each projecting body 8b is not limited to the arc shape and may be appropriately changed in accordance with the shape of the corresponding long hole 22. Although the pair of long holes 22 and the pair of projecting bodies 8b are provided in this embodiment, the numbers of long holes 22 and projecting bodies 8b may be appropriately changed.

On an outer peripheral surface of the base body 8a, a pressing portion 23 projecting radially outward is provided. The pressing portion 23 is provided over an entire circumference in the circumferential direction. The pressing portion 23 is formed of an inclined surface which inclines radially inward toward the proximal end side in the axial direction. The pressing portion 23 may press each pressed portion 21 radially outward by moving toward the proximal end side in the axial direction by an external force applied to the pair of projecting bodies 8b, thereby elastically displacing each engaging convex portion 20 radially outward (in this embodiment, displacing by elastic deformation of the elastic arm 19) (refer to FIG. 7). In this embodiment, since the pressing portion 23 and the pair of pressed portions 21 are both formed of the inclined surfaces inclined radially inward toward the proximal end side in the axial direction, so that such elastic displacement may be stably caused. However, any one of the pressing portion 23 and the pair of pressed portions 21 may be formed of, for example, a step portion a diameter of which is reduced stepwise radially inward toward the proximal end side in the axial direction, for example. Each pressed portion 21 may press the pressing portion 23 toward the distal end side in the axial direction by a restoring force radially inward to move the pressing portion 23 toward the distal end side in the axial direction when the external force to the pair of projecting bodies 8b is eliminated, thereby restoring/displacing each engaging convex portion 20 radially inward (in this embodiment, displacing by restoration/deformation of the elastic arm 19) (refer to FIG. 2).

As illustrated in FIGS. 1 to 3, the proximal tube 6 has a cylindrical shape. On an inner peripheral surface of the proximal tube 6, a pair of spiral grooves 24 having a double-threaded screw shape is provided. The pair of spiral grooves 24 forms a guiding portion which guides a guided portion (a pair of engaging convex portions 20) of the distal tube 4 as the distal tube 4 moves to both the sides in the axial direction. One of the pair of spiral grooves 24 may be engaged with one of the pair of engaging convex portions 20 to guide the one. The other of the pair of spiral grooves 24 may be engaged with the other of the pair of engaging convex portions 20 to guide the other (e.g., cause the pair of engaging convex portions 20 to follow the pair of spiral grooves 24 and simultaneously cause the distal tube to rotate relative to the proximal tube, or vice versa). A lead angle of each spiral groove 24 substantially decreases in a portion engaged with the corresponding engaging convex portion 20 when the engaging convex portion 20 is located on a side the closest to the proximal end in the axial direction. Due to such decrease in the lead angle, it is possible to increase a resistance force when an external force is applied between the proximal tube 6 and the distal tube 4 in a direction of separating them in the axial direction (that is, to make it difficult to loosen a screw). Instead of the decrease in the lead angle, the lead angle may be eliminated (that is, this may be made zero or a negative angle). However, each spiral groove 24 may also have a shape not including such decrease or elimination of the lead angle. The shape of each spiral groove 24 may be appropriately changed in accordance with the shape of the corresponding engaging convex portion 20.

Although the guiding portion is formed of the pair of spiral grooves 24 and the guided portion is formed of the pair of engaging convex portions 20 in this embodiment, the numbers of the spiral grooves 24 and the engaging convex portions 20 may be appropriately increased or decreased. The guiding portion may be formed of a spiral ridge and the guided portion may be formed of an engaging concave portion capable of engaging with the spiral ridge. An entire shape of a track of the guiding portion is not limited to the spiral shape, and may include, for example, a step portion in which the track changes stepwise from the axial direction to the circumferential direction, or may include only the track in the axial direction.

As illustrated in FIG. 1, the proximal tube 6 is provided with a restriction portion 25 which engages with the distal tube 4 to restrict movement of the distal tube 4 toward the proximal end side in the axial direction relative to the proximal tube 6 with a predetermined resistance force. The predetermined resistance force exerted by the restriction portion 25 is preferably larger than the pressing force toward the proximal end side in the axial direction acting from the different medical device 50 on the distal tube 4 from an unconnected state of the different medical device 50 illustrated in FIG. 2 until a standby state illustrated in FIG. 7. With such a configuration, it is possible to stably realize a series of operations of shifting, or transitioning, to a fluid connection state as illustrated in FIG. 8 after the restriction of the restriction portion 25 is released after it is put into the standby state.

Figure 7:
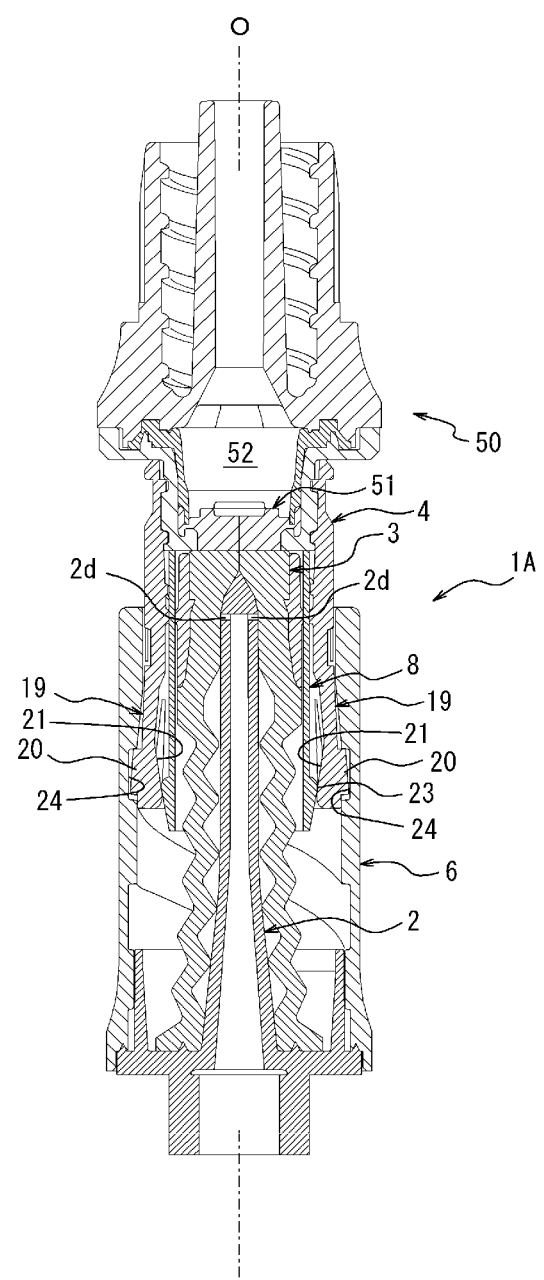
FIG. 7 is a cross-sectional view illustrating the medical device illustrated in FIG. 1 in a standby state.

In this embodiment, as illustrated in FIG. 7, the standby state is intended to mean a state in which the different medical device 50 is connected to the distal tube 4, a different valve body 51 provided on the different medical device 50 abuts the valve body 3, and the spike 2 does not pass through the valve body 3 and the different valve body 51.

Figure 8:
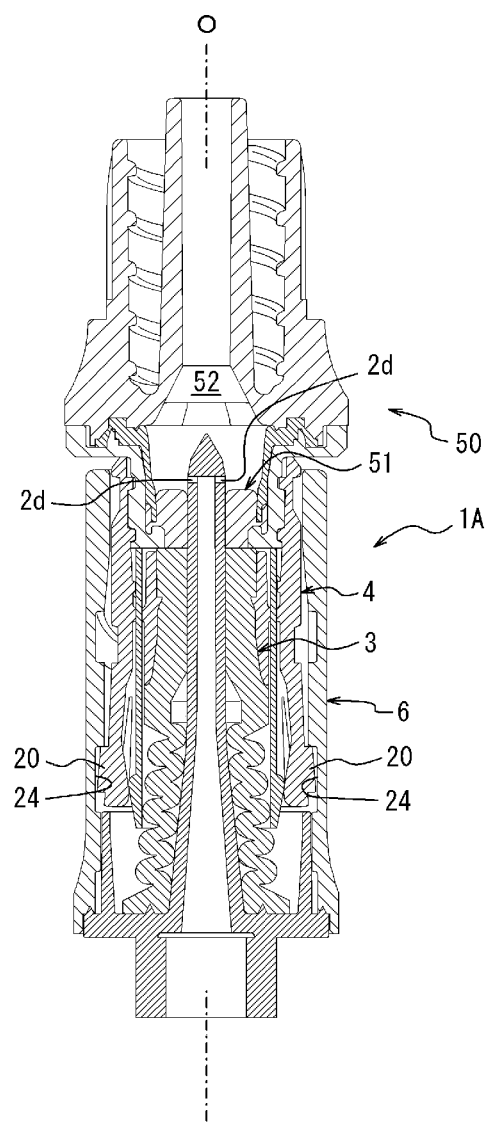
FIG. 8 is a cross-sectional view illustrating the medical device illustrated in FIG. 1 in a fluid connection state.

In this embodiment, the fluid connection state is intended to mean a state in which the different medical device 50 is connected to the distal tube 4, the different valve body 51 abuts the valve body 3, and the spike 2 passes through both the valve body 3 and the different valve body 51 and the communication port 2d is communicated with a different inner flow path 52 provided on the different medical device 50 as illustrated in FIG. 8.

In this embodiment, the restriction portion 25 is formed of a fitting portion capable of fitting to the distal tube 4. More specifically, as illustrated in FIG. 1, the restriction portion 25 is formed of a pair of elastic pieces 27 capable of fitting to a pair of concave portions 26 provided on an outer peripheral surface of the engaging tube 4b of the distal tube 4 and facing each other across the central axis O. One of the pair of elastic pieces 27 may fit to one of the pair of convex portions 26. The other of the pair of elastic pieces 27 may fit to the other of the pair of concave portions 26. Each elastic piece 27 includes an arm portion 27a in a cantilever shape formed on the proximal tube 6 by an inverted U-shaped notch capable of elastically deformed in the radial direction, and a convex portion 27b provided on an inner surface of the arm portion 27a (an inner surface in the radial direction). Each convex portion 27b may exert a predetermined resistance force against the movement of the distal tube 4 toward the proximal end side in the axial direction by fitting to the concave portion 26. Each convex portion 27b may be elastically displaced radially outward (displaced by elastic deformation of the arm portion 27a) when the pressing force toward the proximal end side in the axial direction larger than the predetermined resistance force acts on the distal tube 4, thereby releasing the fitting to the concave portion 26. It is sufficient that each convex portion 27b enters the concave portion 26 to the extent that this may exert the predetermined resistance force against the movement of the distal tube 4 toward the proximal end side in the axial direction, and a gap may be appropriately provided between each convex portion 27b and concave portion 26.

In this embodiment, the restriction portion 25 is formed of a pair of elastic pieces 27 provided on the proximal tube 6 capable of fitting to the pair of concave portions 26 provided on the distal tube 4. However, the configuration of the restriction portion 25 may be appropriately changed. For example, the numbers of the concave portions 26 and the elastic pieces 27 may be appropriately increased or decreased. The distal tube 4 may be provided with one or more elastic pieces 27, and the proximal tube 6 may be provided with one or more concave portions 26.

As illustrated in FIGS. 1 and 2, the different medical device 50 is provided with a housing 53 including the different valve body 51 and the different inner flow path 52. The housing 53 includes a cylindrical tube wall 54. The different valve body 51 is attached to a proximal end of the tube wall 54 so as to close a proximal end of the different inner flow path 52. The different valve body 51 includes a different slit 55 through which the spike 2 may pass. On an outer peripheral surface of the tube wall 54, a connected portion 56 formed of a male screw portion connected to the connecting portion 18 of the distal tube 4 is provided. A shape of the connected portion 56 may be appropriately changed according to the shape of the connecting portion 18. A different connector portion 57 is formed of the tube wall 54 and the different valve body 51. An annular flat abutting surface 58 is provided on a distal end of the different connector unit 57. The abutting surface 58 is configured to abut the distal end face of the engaging tube 4b of the distal tube 4 in the standby state. However, it is possible that the different medical device 50 does not include the abutting surface 58.

The medical device 1A may shift, or transition, from the unconnected state of the different medical device 50 as illustrated in FIG. 2 to the standby state as illustrated in FIG. 7. When shifting to the standby state, the pusher 8 may move toward the proximal end side in the axial direction relative to the distal tube 4 by a pressure from the different medical device 50 in accordance with the connection of the different medical device 50 to the distal tube 4, thereby elastically displacing the guided portion (the pair of engaging convex portions 20) radially outward to allow the same to engage with the proximal tube 6. In this manner, the pusher 8 may move the guided portion radially outward by the connection of the different medical device 50 to the distal tube 4 and allow the same to engage with the proximal tube 6.

The medical device 1A may shift, or transition, from the standby state to the fluid connection state as illustrated in FIG. 8 by a predetermined fluid connection operation. The medical device 1A is configured to shift from the standby state to the fluid connection state when the proximal tube 6 guides the guided portion (the pair of engaging convex portions 20) of the distal tube 4, so that a stable shifting operation from the standby state to the fluid connection state may be performed. In this embodiment, it is possible to shift from the unconnected state to the standby state by a rotational operation in a clockwise direction (right-handed screw direction) and release the restriction by the restriction portion 25 to shift to the fluid connection state by a further rotational operation in the clockwise direction as the predetermined fluid connection operation. In this manner, the medical device 1A may shift from the unconnected state to the fluid connection state only by the rotational operation in one direction. However, it is also possible to configure to use a rotational operation in a counterclockwise direction as the predetermined fluid connection operation.

The medical device 1A may shift, or transition, from the fluid connection state to the standby state by a predetermined releasing operation. The medical device 1A is configured to shift from the fluid connection state to the standby state when the proximal tube 6 guides the guided portion of the distal tube 4, so that a stable shifting operation from the fluid connection state to the standby state may be performed. In this embodiment, it is possible to shift from the fluid connection state to the standby state by a rotational operation in the counterclockwise direction (left-handed screw direction) as the predetermined releasing operation, and shift to the unconnected state by a further rotational operation in the counterclockwise direction. In this manner, the medical device 1A may shift from the fluid connection state to the unconnected state only by the rotational operation in one direction. However, it is also possible to configure to use a rotational operation in the clockwise direction as the predetermined releasing operation.

When shifting, or transitioning, from the standby state to the unconnected state, the pusher 8 may move toward the distal end side in the axial direction so as to allow release of engagement with the proximal tube 6 by the restoration/displacement of the guided portion (the pair of engaging convex portions 20) by release of pressure from the different medical device 50 in accordance with release of connection of the different medical device 50 from the distal tube 4.

Figure 9:
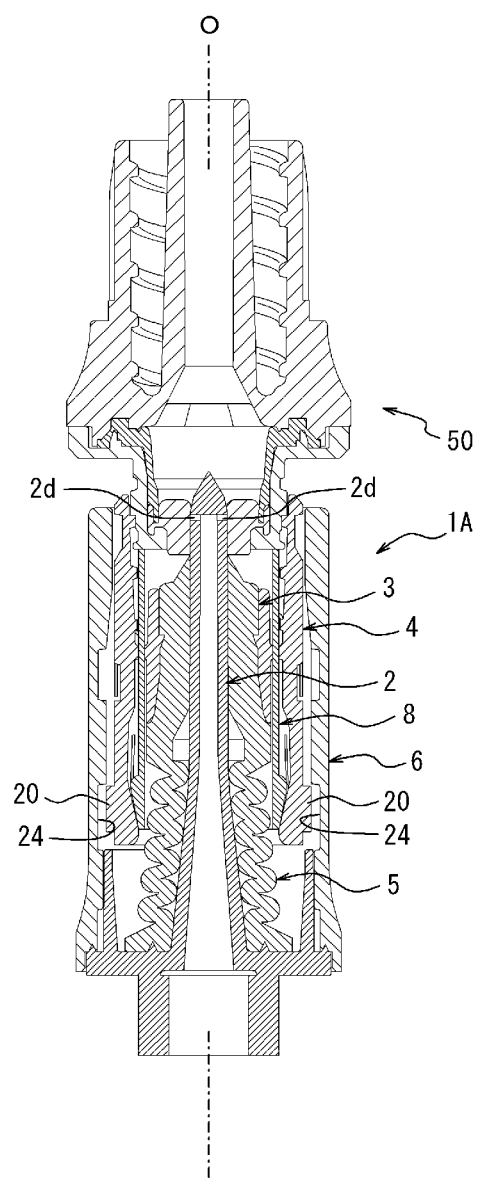
FIG. 9 is a cross-sectional view illustrating an operation when the different medical device is unintentionally detached from the state illustrated in FIG. 8.

In the fluid connection state, when the different medical device 50 is unintentionally detached due to application of an external force in the radial direction or the like, the medical device 1A may allow the release of engagement with the proximal tube 6 by the restoration/displacement of the guided portion (the pair of engaging convex portions 20) by the movement of the pusher 8 toward the distal end side in the axial direction as illustrated in FIG. 9. In this manner, the pusher 8 may move the guided portion radially inward to release the engagement with the proximal tube 6 when the different medical device 50 is detached from the distal tube 4. When the engagement between the guided portion and the proximal tube 6 is released in this manner, the valve body 3 and the distal tube 4 may integrally move toward the distal end side in the axial direction by the biasing force of the biasing body 5, thereby closing the communication port 2d of the spike 2 by the valve body 3 as illustrated in FIG. 2. Therefore, according to the medical device 1A, even when the different medical device 50 is unintentionally detached in the fluid connection state with the different medical device 50, a possibility of exposure of the fluid may be reduced or completely prevented.

Figure 10:
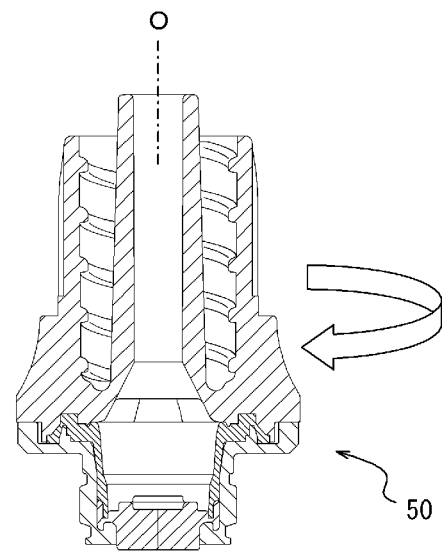
FIG. 10 is a cross-sectional view illustrating a medical device according to a second embodiment of the present disclosure in an unconnected state to a different medical device.
Figure 10:
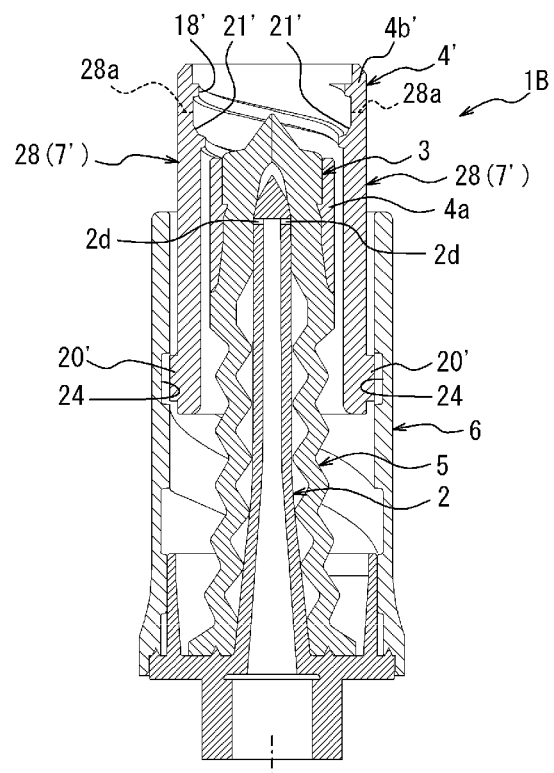
Figure 11:
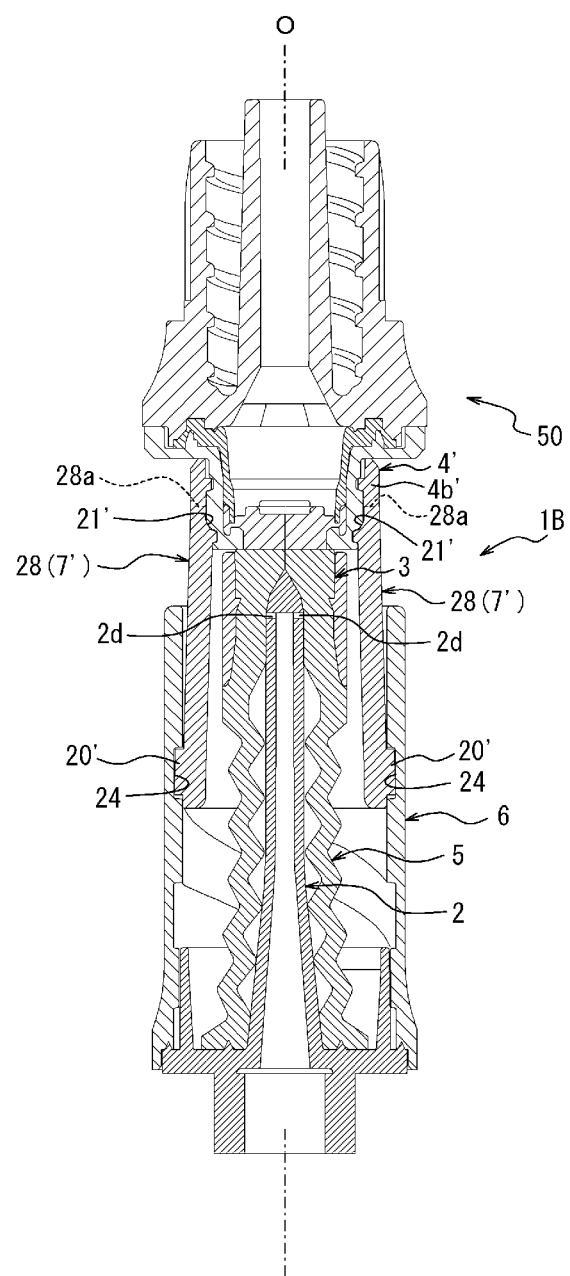
FIG. 11 is a cross-sectional view illustrating the medical device illustrated in FIG. 10 in a standby state.

Next, a medical device according to a second embodiment of the present disclosure is described with an example in detail with reference to FIGS. 10 and 11. The medical device 1A according to the first embodiment described above is provided with the pusher 8 as the engagement control unit 7 which moves the guided portion toward one side in the radial direction by the connection of the different medical device 50 to the distal tube 4 and allows the same to engage with the proximal tube 6, and moves the guided portion toward the other side in the radial direction to release the engagement with the proximal tube 6 when the different medical device 50 is detached from the distal tube 4. In contrast, in a medical device 1B according to the second embodiment, an engaging tube 4b' of a distal tube 4' includes a pair of engaging arms 28 as an engagement control unit 7' in place of the pusher 8 as illustrated in FIG. 10 and FIG. 11. In the second embodiment, a configuration similar to that in the first embodiment is assigned with the same reference numeral as that in the first embodiment.

The pair of engaging arms 28 are arranged so as to face each other across a central axis O. Each engaging arm 28 has a cantilever shape divided by two parallel linear notches extending from a proximal end of the engaging tube 4b' toward a distal end side in an axial direction. Therefore, each engaging arm 28 is rotatable about a fixed end 28a located on a distal end thereof as a fulcrum. On an outer surface (surface on an outer side in the radial direction) of each engaging arm 28, an engaging convex portion 20' projecting radially outward is provided. Each engaging convex portion 20' forms a guided portion guided toward the proximal tube 6 as this moves to both sides in the axial direction. On an inner surface of each engaging arm 28, a pressed portion 21' which projects radially inward is provided on the distal end side in the axial direction relative to a distal end of a holding tube 4a. Each pressed portion 21' is configured to be pressed radially outward by the different medical device 50 along with connection of the different medical device 50 to a connecting portion 18' of the engaging tube 4b' and to be elastically displaced radially outward.

Therefore, by connecting the different medical device 50 to the connecting portion 18' of the engaging tube 4b', the guided portion (the pair of engaging convex portions 20') may be elastically displaced radially outward to be engaged with spiral grooves 24 of the proximal tube 6. It is possible to move the guided portion radially inward and release the engagement with the proximal tube 6 when the different medical device 50 is detached from the engaging tube 4b'. Therefore, an effect similar to that in the first embodiment may also be obtained by the medical device 1B according to this embodiment.

Although a guiding portion is formed of the pair of spiral grooves 24 and the guided portion is formed of the pair of engaging convex portions 20', the numbers of the spiral grooves 24 and the engaging convex portions 20' may be appropriately increased or decreased. The guiding portion may be formed of a spiral ridge and the guided portion may be formed of an engaging concave portion capable of engaging with the spiral ridge. An entire shape of a track of the guiding portion is not limited to the spiral shape, and may include, for example, a step portion in which the track changes stepwise from the axial direction to the circumferential direction, or may include only the track in the axial direction.

Figure 12:
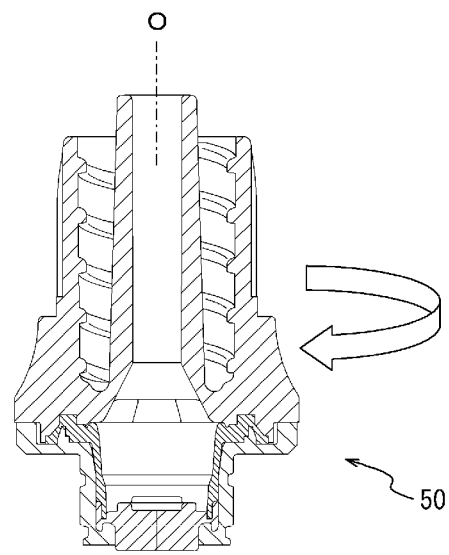
FIG. 12 is a cross-sectional view illustrating a medical device according to a third embodiment of the present disclosure in an unconnected state to a different medical device.
Figure 12:
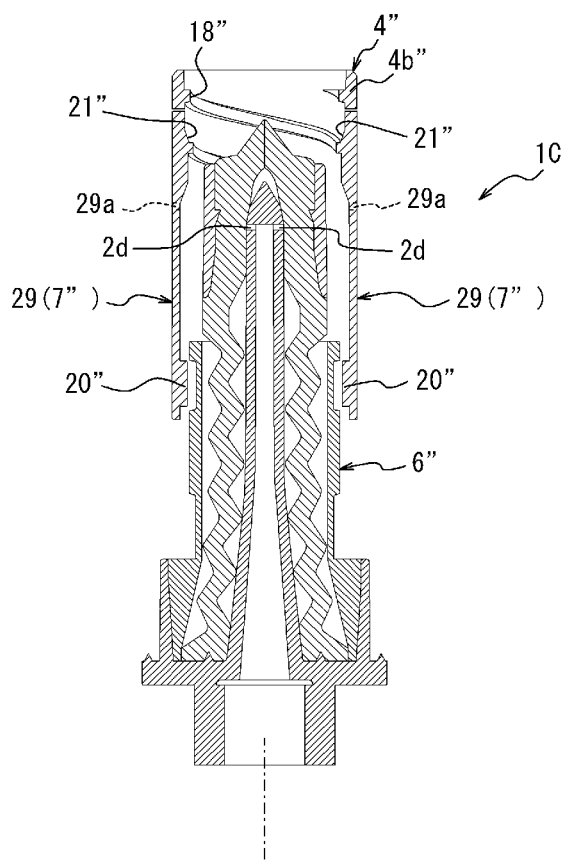
Figure 13:
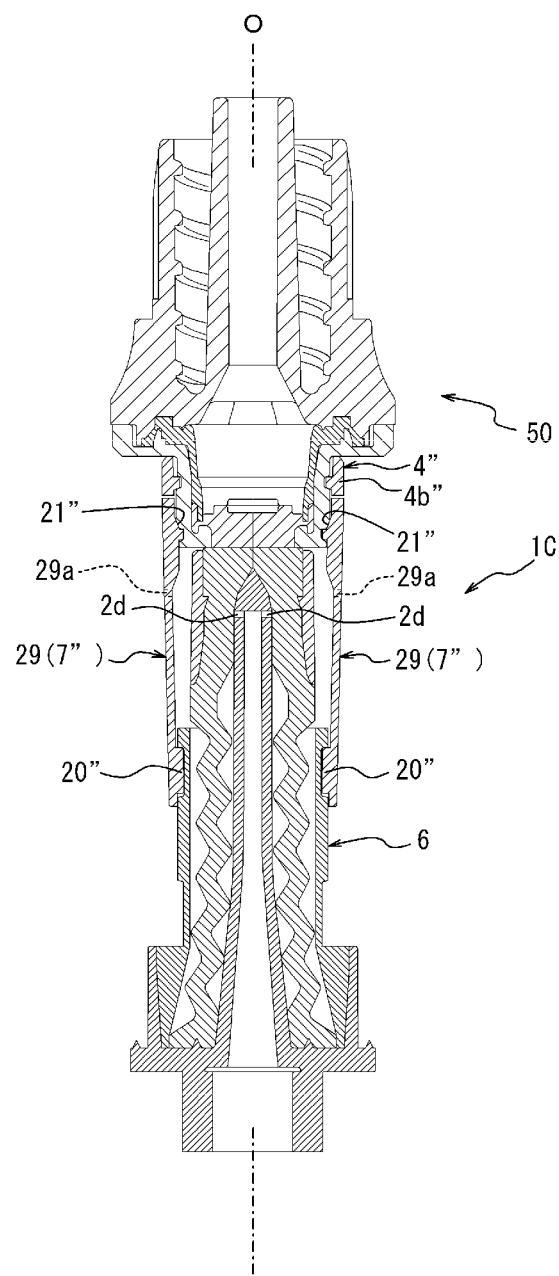
FIG. 13 is a cross-sectional view illustrating the medical device illustrated in FIG. 12 in a standby state.

Next, a medical device according to a third embodiment of the present disclosure is described with an example in detail with reference to FIGS. 12 and 13. In the medical device 1B according to the second embodiment described above, the distal tube 4' is arranged on an inner side in the radial direction than the proximal tube 6. In contrast, in a medical device 1C according to the third embodiment, as illustrated in FIGS. 12 and 13, a distal tube 4" is arranged on an outer side in the radial direction relative to a proximal tube 6". In the third embodiment, a configuration similar to that in the second embodiment is assigned with the same reference numeral as that in the second embodiment.

In this embodiment, an engaging tube 4b" of the distal tube 4" includes a pair of engaging arms 29 as an engagement control unit 7". The pair of engaging arms 29 is arranged so as to face each other across a central axis O. Each engaging arm 29 has a shape of an intermediate-supported swinging piece divided by an inverted U-shaped notch and two parallel linear notches provided below the same with a space and extending to a proximal end of the engaging tube 4b". Therefore, each engaging arm 29 is rotatable about an intermediate portion 29a in an axial direction as a fulcrum. On an inner surface (surface on an inner side in the radial direction) of a portion on a proximal end side from the fulcrum in each engaging arm 29, an engaging convex portion 20" projecting radially inward is provided. Each engaging convex portion 20" forms a guided portion guided toward the proximal tube 6" along with movement to both sides in the axial direction. On an inner surface of a portion on a distal end side relative to the fulcrum in each engaging arm 29, a pressed portion 21" which projects radially inward is provided on the distal end side in the axial direction relative to a distal end of a holding tube 4a. Each pressed portion 21" is configured to be pressed radially outward by the different medical device 50 along with connection of the different medical device 50 to a connecting portion 18" of the engaging tube 4b" and elastically displaced radially outward.

Therefore, by connecting the different medical device 50 to the connecting portion 18" of the engaging tube 4b", the guided portion (a pair of engaging convex portions 20") may be elastically displaced radially inward to be engaged with spiral grooves 24" of the proximal tube 6". It is possible to move the guided portion radially outward and release the engagement with the proximal tube 6" when the different medical device 50 is detached from the engaging tube 4b". Therefore, an effect similar to that in the second embodiment may also be obtained by the medical device 1C according to this embodiment.

In this embodiment, although the guiding portion is formed of a pair of spiral grooves 24" and the guided portion is formed of the pair of engaging convex portions 20", the numbers of the spiral grooves 24" and the engaging convex portions 20" may be appropriately increased or decreased. The guiding portion may be formed of a spiral ridge and the guided portion may be formed of an engaging concave portion capable of engaging with the spiral ridge. An entire shape of a track of the guiding portion is not limited to the spiral shape, and may include, for example, a step portion in which the track changes stepwise from the axial direction to the circumferential direction, or may include only the track in the axial direction.

The embodiments described above are merely an example of the embodiments of the present disclosure, and it goes without saying that various changes may be made without departing from the gist of the disclosure.

What is claimed is:

1. A medical device comprising:
   a spike including a proximal end, a distal end, a central axis extending from the proximal end to the distal end, and an inner flow path;
   a valve body through which the spike is able to pass;
   a biasing body which biases the valve body toward a side of the distal end in an axial direction along the central axis;
   a distal tube to which a different medical device is able to be connected, the distal tube configured to move integrally with the valve body to both sides in the axial direction relative to the spike;
   a proximal tube fixed in the axial direction relative to the spike,
   wherein the distal tube comprises a guided portion guided toward the proximal tube along with movement to both the sides in the axial direction; and
   an engagement control unit which moves the guided portion toward a first side in a first radial direction by connection of the different medical device to the distal tube to allow the guided portion to engage with the proximal tube, and moves the guided portion toward a second side opposite the first side in a second radial direction opposite the first radial direction to release engagement with the proximal tube when the different medical device is detached from the distal tube.

2. The medical device of claim 1, wherein the distal tube is arranged on an inner side disposed radially inward relative to an outer surface of the proximal tube.

3. The medical device of claim 1, further comprising:
   a pusher configured to move to both the sides in the axial direction relative to the distal tube as the engagement control unit, wherein the pusher elastically displaces the guided portion radially outward from the central axis to allow the guided portion to engage with the proximal tube by moving to a side of the proximal end in the axial direction relative to the distal tube by pressure from the different medical device along with the connection of the different medical device to the distal tube.

4. The medical device of claim 1,
wherein the different medical device includes a different valve body and a different inner flow path,
wherein the medical device is configured to shift from a standby state in which the different medical device is connected to the distal tube, the different valve body abuts the valve body, and the spike does not pass through the valve body and the different valve body to a fluid connection state in which the different medical device is connected to the distal tube, the different valve body abuts the valve body, and the spike passes through both the valve body and the different valve body and the inner flow path is in communication with the different inner flow path by a predetermined fluid connection operation, and
wherein the medical device is configured to shift from the fluid connection state to the standby state by a predetermined releasing operation.

5. The medical device of claim 4, wherein the proximal tube guides the guided portion toward the side of the proximal end in the axial direction by a rotational operation to a first side in a first circumferential direction about the central axis as the predetermined fluid connection operation, and guides the guided portion toward the side of the distal end in the axial direction by a rotational operation to a second side opposite the first side in a second circumferential direction opposite the first circumferential direction as the predetermined releasing operation.

6. The medical device of claim 2, further comprising:
a pusher configured to move to both the sides in the axial direction relative to the distal tube as the engagement control unit,
wherein the pusher elastically displaces the guided portion radially outward from the central axis to allow the guided portion to engage with the proximal tube by moving to a side of the proximal end in the axial direction relative to the distal tube by pressure from the different medical device along with the connection of the different medical device to the distal tube.

7. The medical device of claim 2,
wherein the different medical device includes a different valve body and a different inner flow path,
the medical device is configured to shift from a standby state in which the different medical device is connected to the distal tube, the different valve body abuts the valve body, and the spike does not pass through the valve body and the different valve body to a fluid connection state in which the different medical device is connected to the distal tube, the different valve body abuts the valve body, and the spike passes through both the valve body and the different valve body and the inner flow path is communicated with the different inner flow path by a predetermined fluid connection operation, and
wherein the medical device is configured to shift from the fluid connection state to the standby state by a predetermined releasing operation.

8. The medical device of claim 3, wherein the different medical device includes a different valve body and a different inner flow path,
wherein the medical device is configured to shift from a standby state in which the different medical device is connected to the distal tube, the different valve body abuts the valve body, and the spike does not pass through the valve body and the different valve body to a fluid connection state in which the different medical device is connected to the distal tube, the different valve body abuts the valve body, and the spike passes through both the valve body and the different valve body and the inner flow path is communicated with the different inner flow path by a predetermined fluid connection operation, and
wherein the medical device is configured to shift from the fluid connection state to the standby state by a predetermined releasing operation.

9. A medical device assembly comprising:
a first medical device, comprising:
a spike including a proximal end, a distal end, a central axis extending from the proximal end to the distal end, and an inner flow path;
a valve body through which the spike is able to pass;
a biasing body which biases the valve body toward a side of the distal end in an axial direction along the central axis;
a distal tube configured to move integrally with the valve body to both sides in the axial direction relative to the spike, the distal tube comprising a guided portion;
a proximal tube fixed in the axial direction relative to the spike and comprising guides that engage with the guided portion of the distal tube and guide a movement of the distal tube in the axial direction; and
an engagement control unit that moves in the axial direction relative to the spike; and
a second medical device that connects with the distal tube and when connected to the distal end the engagement control moves the guided portion of the distal tube toward the guides of the proximal tube in a radial direction allowing the guided portion to engage with the guides of the proximal tube and when detached from the distal tube the engagement control unit moves axially allowing the guided portion of the distal tube to disengage from the guides of the proximal tube.

10. The medical device assembly of claim 9, wherein the distal tube is arranged on an inner side radially inward relative to the proximal tube.

11. The medical device assembly of claim 9, wherein the first medical device further comprises:
a pusher configured to move to both the sides in the axial direction relative to the distal tube as the engagement control unit,
wherein the pusher elastically displaces the guided portion radially outward from the central axis to allow the guided portion to engage with the guides of the proximal tube by moving to a side of the proximal end in the axial direction relative to the distal tube by pressure from the second medical device along with the connection of the second medical device to the distal tube.

12. The medical device assembly of claim 9, wherein the second medical device includes a second valve body and a second inner flow path,
wherein the first medical device is configured to transition from a standby state in which the second medical device is connected to the distal tube, the second valve body abuts the valve body, and the spike does not pass through the valve body and the second valve body to a fluid connection state in which the second medical device is connected to the distal tube, the second valve body abuts the valve body, and the spike passes through both the valve body and the second valve body and the inner flow path is in fluid communication with the second inner flow path by a predetermined fluid connection operation, and wherein the first medical device is configured to transition from the fluid connection state to the standby state by a predetermined releasing operation.

13. The medical device assembly of claim 12, wherein the proximal tube guides the guided portion toward the side of the proximal end in the axial direction by a rotational operation to a first side in a first circumferential direction about the central axis as the predetermined fluid connection operation, and guides the guided portion toward the side of the distal end in the axial direction by a rotational operation to a second side opposite the first side in a second circumferential direction opposite the first circumferential direction as the predetermined releasing operation.

14. The medical device assembly of claim 10, wherein the first medical device further comprises:
a pusher configured to move to both the sides in the axial direction relative to the distal tube as the engagement control unit,
wherein the pusher elastically displaces the guided portion radially outward from the central axis to allow the guided portion to engage with the guides by moving to a side of the proximal end in the axial direction relative to the distal tube by pressure from the second medical device along with the connection of the second medical device to the distal tube.

15. The medical device assembly of claim 10, wherein the second medical device further comprises a second valve body and a second inner flow path,
wherein the first medical device is configured to transition from a standby state in which the second medical device is connected to the distal tube, the second valve body abuts the valve body, and the spike does not pass through the valve body and the second valve body to a fluid connection state in which the second medical device is connected to the distal tube, the second valve body abuts the valve body, and the spike passes through both the valve body and the second valve body and the inner flow path is communicated with the second inner flow path by a predetermined fluid connection operation, and wherein the first medical device is configured to transition from the fluid connection state to the standby state by a predetermined releasing operation.

16. The medical device assembly of claim 11, wherein the second medical device includes a second valve body and a second inner flow path,
wherein the first medical device is configured to transition from a standby state in which the second medical device is connected to the distal tube, the second valve body abuts the valve body, and the spike does not pass through the valve body and the second valve body to a fluid connection state in which the second medical device is connected to the distal tube, the second valve body abuts the valve body, and the spike passes through both the valve body and the second valve body and the inner flow path is communicated with the second inner flow path by a predetermined fluid connection operation, and wherein the first medical device is configured to transition from the fluid connection state to the standby state by a predetermined releasing operation.

17. A medical device comprising:
a cylindrical spike extending along a central axis from a proximal end to a distal end and comprising an internal flow path and a fluid communication port passing through cylindrical spike into the internal flow path;
a valve body disposed circumferentially around at least a portion of the cylindrical spike;
a biasing body contacting the valve body and configured to bias the valve body toward the distal end;
a distal tube that selectively connects with a different medical device, the distal tube configured to move with the valve body in a direction defined by the central axis of the cylindrical spike;
a proximal tube axially fixed to a proximal portion of the cylindrical spike and disposed radially outward from the central axis surrounding the proximal end of the cylindrical spike, wherein the distal tube is disposed at least partially inside a hollow portion of the proximal tube between an inner surface of the proximal tube and an outer surface of the cylindrical spike;
an engaging projection disposed on a proximal end of the distal tube and extending radially outward from an outer surface of the distal tube in a direction toward the inner surface of the proximal tube, wherein the engaging projection is movable between an engaged state with guides in the proximal tube when the different medical device is connected to the distal tube elastically compressing the biasing body toward the proximal end of the cylindrical spike and moving the valve body axially past the fluid communication port and a disengaged state from the guides in the proximal tube when the different medical device is detached from the distal tube elastically releasing the biasing body toward the distal end moving the valve body covering the fluid communication port.

18. The medical device of claim 17, wherein the engaging projection comprises a plurality of convex portions projecting from the outer surface of the distal tube.

19. The medical device of claim 18, wherein the proximal tube comprises a plurality of spiral groove portions disposed on the inner surface of the proximal tube, and wherein the plurality of spiral groove portions receive the plurality of convex portions when the engaging projection is in the engaged state.

20. The medical device of claim 19, wherein the different medical device comprises a different valve body and a different inner flow path,
wherein in the engaged state, the different medical device is connected to the distal tube and a fluid communication channel is formed running from the internal flow path to the different inner flow path of the different valve body defining a fluid connection state of the medical device.

* * * * *